US012168783B2

United States Patent
Michaeli et al.

(10) Patent No.: US 12,168,783 B2
(45) Date of Patent: *Dec. 17, 2024

(54) ONCODIALYSIS SYSTEM AND METHOD FOR PERSONALIZED AUTOLOGOUS CANCER VACCINE AND BLOOD PURIFICATION

(71) Applicants: David Michaeli, Ashkelon (IL); Menashe Michaeli, Ashkelon (IL)

(72) Inventors: David Michaeli, Ashkelon (IL); Menashe Michaeli, Ashkelon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,909

(22) Filed: Oct. 17, 2023

(65) Prior Publication Data

US 2024/0327798 A1    Oct. 3, 2024

Related U.S. Application Data

(63) Continuation-in-part of application No. 18/129,866, filed on Apr. 2, 2023, now Pat. No. 12,042,590.

(51) Int. Cl.
*C12N 5/09* (2010.01)
*C12M 1/00* (2006.01)
(Continued)

(52) U.S. Cl.
CPC ........... *C12N 5/0694* (2013.01); *C12M 33/14* (2013.01); *C12M 35/02* (2013.01); *C12M 47/10* (2013.01); *C12N 13/00* (2013.01)

(58) Field of Classification Search
CPC .... A61M 1/34; A61M 1/3681; A61M 1/3472; A61M 2205/053; A61M 2202/021; A61M 2202/0413; A61M 2210/12
See application file for complete search history.

(56) References Cited

U.S. PATENT DOCUMENTS

| 4,464,168 A | 8/1984 | Redmond et al. |
| 5,480,552 A * | 1/1996 | Soltys ............... B01D 61/147 |
| | | 210/645 |

(Continued)

FOREIGN PATENT DOCUMENTS

| CN | 107233076 B | 2/2018 |
| CN | 108267416 A | 7/2018 |

(Continued)

OTHER PUBLICATIONS

Park H, Gladstone M, Shanley C Goodrich R, and Guth A. A novel cancer immunotherapy utilizing autologous tumor tissue. Vox Sanuinis 115, 525-535 (2020). (Year: 2020).*

(Continued)

*Primary Examiner* — Leslie R Deak
(74) *Attorney, Agent, or Firm* — Shlomo Horowitz; Shlomo Horowitz Patents and Intellectual Property Ltd.

(57) ABSTRACT

A system and method for preparing a cancer vaccine (and optionally purifying the blood) has a blood filtration system, controlled by a processing unit, for filtering exogenous blood plasma to isolate tumor cells, tumor stem cells and tumor breakdown products. The blood filtration system filter may include multiple layers having differently sized apertures to retain differently sized materials (from among tumor cells of different sizes, tumor stem cells and tumor breakdown products. A device directs electromagnetic radiation at the separated tumor cells, tumor stem cells and/or tumor breakdown products. The electromagnetic radiation may cause the separated tumor cells, separated tumor stem cells and/or separated tumor breakdown products (for example tumor protein such as DNA and/or tumor exosomes) to have a coagulated outer layer such as by degrading the outer surface. The electromagnetic radiation may have a UV (Continued)

wavelength. A conical coil improves flow rate uniformity. Tumor exosomes may be centrifuged.

28 Claims, 6 Drawing Sheets

(51) Int. Cl.
*C12M 1/26* (2006.01)
*C12M 1/42* (2006.01)
*C12N 13/00* (2006.01)

(56) References Cited

U.S. PATENT DOCUMENTS

| | | | |
|---|---|---|---|
| 10,660,565 | B2 | 5/2020 | Myslinski |
| 10,918,782 | B1 * | 2/2021 | Ishak ................ A61M 1/3482 |
| 2004/0009195 | A1 | 1/2004 | Jennings et al. |
| 2013/0131423 | A1 | 5/2013 | Wang et al. |
| 2013/0204101 | A1 | 8/2013 | Rumberg |
| 2015/0371019 | A1 | 12/2015 | Romanick |
| 2018/0264132 | A1 | 9/2018 | Michaeli |
| 2020/0064258 | A1 | 2/2020 | Son et al. |
| 2023/0166020 | A1 * | 6/2023 | Moroz ................ A61M 1/3687 604/6.01 |

FOREIGN PATENT DOCUMENTS

| | | |
|---|---|---|
| CN | 108627466 A | 10/2018 |
| CN | 108728414 A | 11/2018 |
| WO | WO2017044723 A | 3/2016 |
| WO | WO2019074187 A | 4/2019 |

OTHER PUBLICATIONS

Liu Yu, The Medical Application of Terahertz Technology in NOn-invasive detection of cells and tissues: opportunities and challenges, Mar. 22, 2019, RSC ADV, 2019, 9354-9363.

Tami Freedman, THz Technology: a new take on cancer imaging, PhysicsWorld, Aug. 7, 2018.

Kohei Kuroda, Thr Safety and Anti-tumor Effects of Ozonated Water In Vivo, Int. J. Mol, Sci. 2015, 16(10), 25108-25120.

The Optical Society, New Terahertz IMaging Approach Could Speed Up Skin Cancer Detection, ScienceDaily, Aug. 17, 2017.

* cited by examiner

ONCODIALYSIS SYSTEM AND METHOD FOR PERSONALIZED AUTOLOGOUS CANCER VACCINE AND BLOOD PURIFICATION

FIELD OF THE INVENTION

The embodiments described herein generally relate to systems and methods for cleaning a mammalian subject's blood of cancerous elements and/or implementing an onco-dialysis system or method, and more particularly, to systems and methods for separating out tumor cells, tumor stem cells and/or tumor breakdown products (components) thereof from the subject's exogenous blood or other body fluid and modifying (reprogramming) these tumor cells, tumor stem cells and/or tumor breakdown products to create a personalized cancer vaccine for the subject that can then be injected or otherwise delivered into the subject.

BACKGROUND

In general although great strides have been made against the disease of cancer, it is still a dreaded disease. In addition, some of the treatments—for example chemotherapy-cause damaging side effects. In addition, chemotherapy does not typically have a high rate of success for advanced-stage—such as stage 4 cancer patients.

In some approaches to fighting cancer, tumor cells from the patient are injected to animals such as mice to induce the mice to produce antibodies—for example monoclonal antibodies—against these tumor cells, and then injecting the antibodies into the patient. This approach causes undesirable side-effects such allergic reactions in which the patient's immune system recognizes the antibody as foreign (since the mice antibodies contain foreign animal protein and are not necessarily compatible with the patient's body's immune system). Besides the side-effects of auto-immune disorders or even autism, the level of affinity is not great enough to reliably provoke the immune responses needed to successfully attack the cancer tumors.

There have been efforts to modify or humanize these animal antibodies by making the protein sequences more similar to antibodies produced in humans by a person who has the same type of cancer. For example, humanization of murine monoclonal antibodies has been performed through replacement of mouse constant regions and V framework regions for human sequences. However, it has been recognized that although this is a significant improvement over murine antibodies in terms of in vivo tolerability, "some humanized and even fully human sequence-derived antibody molecules still carry immunological risk." See "The immunogenicity of humanized and fully human antibodies", MAbs, 2010 May-June; 2(3): 256-265 at Abstract https://www.ncbi.nlm.nih.gov/pmc/articles/PMC2881252/#:~:text=Humanization%20of%20murine%20monoclonal%20antibodies.a%20significantly%20less%20immunogenic%20product.

SUMMARY OF THE EMBODIMENTS

One embodiment is a system for preparing an autologous cancer vaccine for a mammalian subject whose blood has a tumor entity circulating, comprising: a blood filtration system for filtering exogenous blood plasma to separate out an oncological component, the oncological component made up primarily of at least one of (i) tumor cells, (ii) tumor stem cells and (iii) tumor breakdown products, the oncological component not configured to be recognized as an antigen by an immune system of the subject; at least one device for directing electromagnetic radiation at the separated oncological component so as to convert an outer surface of the at least one of the (i) separated tumor cells, (ii) separated tumor stem cells and (iii) separated tumor breakdown products into a coagulated outer layer and thereby convert the oncological component to something that the immune system of the subject will recognize as the antigen when reinserted into the subject's body, the electromagnetic radiation having a UV wavelength; and a processing unit configured to control the blood filtration system.

In some embodiments, the separated out oncological component has only a remnant of the blood plasma that is less than about 5% by volume of the separated out oncological component.

In some embodiments, the separated out oncological component has only a remnant of the blood plasma that is less than about 1% by volume of the separated out oncological component.

In some embodiments, the separated out oncological component has only a remnant of the blood plasma that is less than about 0.5% by volume of the separated out oncological component.

In some embodiments, the separated out oncological component has only a remnant of the blood plasma that is less than about 0.1% by volume of the separated out oncological component.

In some embodiments, the separated out oncological component comprises at least two of (i) the separated tumor cells, (ii) the separated tumor stem cells and (iii) the separated tumor breakdown products.

In some embodiments, the separated out oncological component comprises (i) the separated tumor cells, (ii) the separated tumor stem cells and (iii) the separated tumor breakdown products.

In some embodiments, the separated out oncological component comprises the separated tumor breakdown products, wherein the separated tumor breakdown products comprises tumor exosomal peptides.

Another embodiment is a method of preparing a vaccine against cancer for a mammalian subject using components of exogenous blood of the subject, the method comprising: (a) filtering exogenous blood plasma of the exogenous blood of the subject to separate out an oncological component that is made up primarily of at least one of tumor cells, tumor stem cells and tumor breakdown products, the oncological component not configured to be recognized as an antigen by an immune system of the subject; and (b) directing electromagnetic radiation at the separated oncological component, so as to degrade and thereby convert an outer surface of the at least one of the separated tumor cells, separated tumor stem cells and separated tumor breakdown products into a coagulated outer surface and thereby convert the oncological component into something that the immune system will recognize as the antigen when reinserted into the subject's body; and (c) using a processing unit to control the filtering of the blood plasma.

In some embodiments, the separated out oncological component has only a remnant of the blood plasma that is less than about 5% by volume of the separated out oncological component.

In some embodiments, the separated out oncological component has only a remnant of the blood plasma that is less than about 1% by volume of the separated out oncological component.

In some embodiments, the separated out oncological component has only a remnant of the blood plasma that is less than about 0.5% by volume of the separated out oncological component.

In some embodiments, the separated out oncological component has only a remnant of the blood plasma that is less than about 0.1% by volume of the separated out oncological component.

In some embodiments, the method further comprises separating tumor exosomes from the exogenous blood plasma by a step by step centrifuging process after separating out the oncological component from the exogenous blood plasma.

In some embodiments, the method further comprises degrading one or more layers of water surrounding the outer surface of the least one of the separated tumor cells, separated tumor stem cells and separated tumor breakdown products.

In some embodiments, the electromagnetic radiation has wavelengths in an ultraviolet (UV) range.

In some embodiments, the UV radiation comprises UVC radiation.

In some embodiments, the method further comprises irradiating the at least one of the separated tumor cells, separated tumor stem cells and separated tumor breakdown products with electromagnetic radiation of up to 0.1 terahertz.

In some embodiments, the method further comprises after directing electromagnetic radiation at the separated oncological component, injecting at least one of the separated tumor cells, separated tumor stem cells and separated tumor breakdown products into the subject to induce the subject's immune system to produce autologous antibodies in reaction to the coagulated outer surface of the at least one of the separated tumor cells, separated tumor stem cells and separated tumor breakdown products.

In some embodiments, the method further comprises separating out the oncological component from the blood plasma using a filter that has multiple layers, each layer having differently sized apertures to retain differently-sized materials from among (i) one or more sizes of the tumor cells, (ii) the tumor stem cells and (iii) the tumor exosomes.

In some embodiments, the filtering utilizes a filter that has an outer layer configured to retain the tumor cells, the outer layer having apertures of a first diameter and has a second layer configured to retain the tumor stem cells, the second layer having apertures of a second diameter smaller than the first diameter.

In some embodiments, the filter further comprises an inner layer configured to retain the separated tumor exosomes and apertures of a third diameter smaller than the second diameter.

In some embodiments, the separated out oncological component comprises at least two of (i) the separated tumor cells, (ii) the separated tumor stem cells and (iii) the separated tumor breakdown products.

In some embodiments, the separated out oncological component comprises (i) the separated tumor cells, (ii) the separated tumor stem cells and (iii) the separated tumor breakdown products. In some embodiments, the separated tumor breakdown products comprises tumor exosomal peptides.

BRIEF DESCRIPTION OF THE DRAWINGS

Various embodiments are herein described, by way of example only, with reference to the accompanying drawings, wherein.

DETAILED DESCRIPTION OF THE EMBODIMENTS

Figure 1:
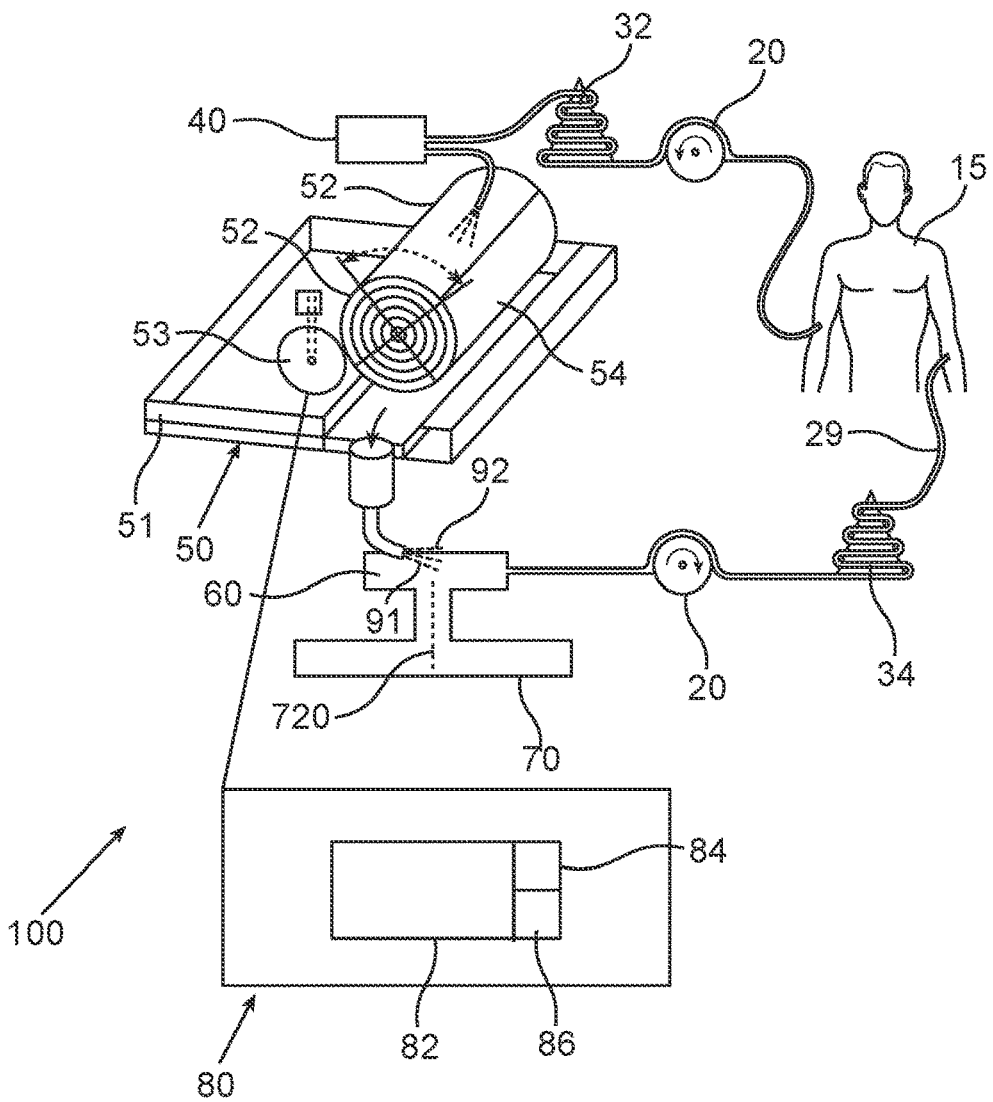
FIG. 1 is a schematic view of an oncodialysis system, in accordance with one embodiment.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Applicant has understood that even antibodies, such as monoclonal antibodies, that have been humanized by incorporating protein sequences found in human antibodies of a person afflicted with the exact same type of cancer may well not be fully compatible with the patient because even a specific type of cancer (for example glioblastoma) exhibits variability from one person to another. The antibodies made by the other person are therefore of insufficient affinity.

Applicant is therefore using an entirely different approach, namely to make an individualized custom-tailored personalized vaccine. This approach involves, in certain embodiments, taking the blood of the patient that contains circulating tumor cells, tumor stem cells and tumor breakdown products (such as DNA, protoplasm etc.) of these tumor cells and tumor stem cells that are also circulating in the blood, and isolating them and reprogramming them to induce the patient's immune system to recognize them as foreign bodies so as to generate antibodies by the patient against these "foreign" reprogrammed tumor cells, tumor stem cells and/or tumor cell breakdown products. Accordingly, a vaccine is created that is customized exactly to the patient in certain embodiments. Furthermore, in some embodiments, the blood of the patient has been cleaned in some embodiments since it has been purified of the circulating tumor cells, tumor stem cells and tumor DNA and other breakdown products. The purified blood, is therefore fit to be recirculated back into the veins of the patient and as a result from the purification process alone the patient has a much lower risk of metastasis.

Certain embodiments generally provide a system and method for preparing a cancer vaccine for a mammalian subject using oncodialysis. When a tumor metastasizes, cells from the tumor move into the blood of the patient (as well as into certain nearby lymph nodes). In preparation for (or pursuant to, in some embodiments of the method) the system and method, blood containing circulating tumor cells and circulating tumor stem cells are removed from the patient's blood—for example about 40 cc at a time or in other embodiments about 200 ccs at a time—for example using a peristaltic pump connected by tubing to the veins of the patient (i.e. one arm of the patient), or by another method. A peristaltic pump may include a mechanism for inducing blood circulation. In certain embodiments, since the blood movement is not uniform, since it moves by pulsation due to the peristaltic pump, a damper, for example at least one conically arranged or shaped coil downstream of the pump, is used to maintain smooth flow of the blood (by increasing a degree of uniformity of the rate of the blood flow). After passing through the coil or damper, the exogenous blood may continue into a container, for example a blood reservoir, from which it travels in some embodiments through an inlet of a blood filtration system into the blood filtration system. The exogenous blood referred to herein is autologous.

The blood filtration system is configured to isolate at least one of (or in other embodiments at least two of or all three of) tumor cells, tumor stem cells and tumor breakdown products from the exogenous blood plasma (the exogenous blood plasma itself having been filtered from the exogenous blood of the subject), for example using a filter which may have multiple layers. In some embodiments, the system is also configured, as a preliminary step, to isolate the blood plasma from the exogenous blood of the subject.

Part of the filtration process may also involve subjecting the filtered material—for example cells—to an evaluation to determine if they are tumor cells or not. Such a procedure may include staining the cells that were too large to traverse a particular layer of the filter and then looking at these cells under a microscope to determine if they are indeed cancerous. In some embodiments, this oncological identification step is automated. In some embodiments, this oncological identification step is performed by a human operator or doctor.

After being filtered in the blood filtration system, the at least one of the separated out tumor cells, separated out tumor stem cells and separated out tumor breakdown products such as tumor protein (i.e. tumor protein, tumor peptides, tumor exosomal peptides, tumor DNA or tumor DNA pieces such as tumor RNA or other pieces that were inside the tumor cells), are reprogrammed. This may occur in a container although this is not a limitation.

As part of the reprogramming, these isolated or separated out products may be subjected to electromagnetic radiation, such as electromagnetic radiation at a UV wavelength, for about five to about nine seconds (or an amount in between). Other procedures are used in the reprogramming step such as hydrogenated water, ozone, freezing. These reprogrammed isolated components are then fit to be injected (or otherwise delivered) into the patient's muscle. The purified blood is fit to be recirculated or reintroduced into the patient, for example through veins of an arm of the patient (different from the arm through which the blood was originally drawn). In some embodiments, the recirculation occurs after passing the purified blood through a further peristaltic pump and at least one further conically arranged coil.

During the reprogramming, the electromagnetic radiation causes the outer layer of the isolated component(s) (tumor cells, tumor stem cells and tumor cell breakdown products such as tumor DNA and tumor protoplasm) to coagulate. Furthermore, in some embodiments, the blood itself has been cleaned of all (or virtually all) of the circulating (metastasizing) tumor cells and circulating tumor stem cells and their respective components.

The reprogrammed components circulating in the blood within the patient's body, having a coagulated outer layer, are recognized by the patient's immune system as foreign bodies or foreign proteins, i.e. antigens, since the patient's immune system does not recognize these coagulated outer layers as being the outer surface of any protein or cell that is recognizes from the patient's body. The patient's immune system is therefore triggered to produce autologous antibodies that attack the reprogrammed tumor cells, reprogrammed tumor stem cells and/or reprogrammed tumor cell breakdown products such as reprogrammed tumor proteins, tumor peptides, tumor exosomal peptides or tumor DNA (these are non-limiting examples of tumor breakdown products).

The phrase "tumor breakdown products" (as well as the phrase "tumor cell breakdown products") as used herein refers to one or more components of tumor cells or tumor stem cells that have broken off from the tumor cell or tumor stem cell. Examples include tumor DNA, tumor protoplasm, tumor protein, tumor peptides and other breakdown products of tumor cells or tumor stem cells. "Breakdown products of tumor cells" as used herein refers to tumor breakdown products that are from tumor cells. "Breakdown products of tumor stem cells" as used herein refers to tumor breakdown products that are from tumor stem cells. "Reprogrammed tumor breakdown products" as used herein means one or more tumor breakdown products that have been reprogrammed with respect to their outer surface by one or more procedures described herein (for example the application of electromagnetic radiation).

In this patent application, the word "isolated" means separated and the phrase "to isolate" means to separate. Therefore, that which is described herein as "isolated" (separated) is not necessarily something that exists alone, in solitude.

Examples of tumor protein, which are also examples of tumor peptides, include exosomes of tumor cells and exosomes of tumor stem cells. These exosomes of tumor cells and tumor stem cells are herein collectively referred to as "tumor exosomes" or "tumor exosomal peptides" or "tumor exosomal proteins". Since they circulate in the subject's blood reinjection of the reprogrammed tumor entities, in some embodiments herein, they are also sometimes referred to as "circulating tumor exosomal peptides".

In some embodiments, one of the advantages of the system 10, 100 and methods 200, 300, 400 described herein is the multicomponental nature of the reprogramming, which (upon reinsertion into the subject's body such as by reinjection) draws attacks by the subject's immune system against different tumor components. This generates a broader range of multivariate antibodies which together are more likely to overpower the cancer in the subject's body (than if only one tumor element were used to trigger production of antibodies). For example, the variety of tumor components may include tumor cells, tumor stem cells, tumor breakdown products and the tumor breakdown products may include tumor exosomes. This means a variety of tumor entities are drawing attacks from a variety of antibodies.

One way that cancer cells evade the body's immune system that would otherwise attack the cancer cells is by producing proteins (called checkpoint proteins) on their surface that signal to the immune system cells that the cancer cells are normal cells of the body and not foreign invaders. In contrast, in certain embodiments of the system and method, due to the reprogramming of the tumor cells, tumor stem cells and tumor breakdown products (such as tumor DNA, tumor protoplasm or other tumor breakdown products) in which their outer surface becomes a coagulated layer or coagulated outer surface, the patient's body does attack the tumor cells, the tumor stem cells and the tumor breakdown products (such as tumor DNA, tumor protoplasm or other breakdown products of the tumor cells or the tumor stem cells). Moreover, in some embodiments, without being bound by theory, the coagulation removes the possibility of producing proteins on the surface of the tumor cells and on the surface of tumor stem cells that signal that the cell is a normal cell so as to evade the body's immune system. The reprogrammed tumor cells, tumor stem cells and tumor cell breakdown products (such as tumor DNA, tumor protoplasm and other breakdown products of the tumor cells and tumor stem cells) are therefore the active ingredients of a cancer vaccine that has been customized to the specific patient.

Furthermore, once the body's immune system creates autologous antibodies that target the reprogrammed tumor cells, reprogrammed tumor stem cells and reprogrammed DNA, exosomal peptides (and other breakdown products of the tumor cells), Applicant believes that these autologous antibodies (or other parts of the patient's immune system) will also attack future newly created tumor cells, tumor stem cells and newly created breakdown products that break off from the tumor, metastasize and circulate in the patient's blood (after any cleaning of the blood and reinjection of reprogrammed tumor entities).

There may be a number of reasons for this. Without being limited by the theory, one non-limiting example of such a reason is that when the antibodies attack the reprogrammed tumor cells these attacked tumor cells break apart and the protein—for example DNA—inside them falls out. The body then also attacks the mutated tumor DNA and develops further antibodies for these mutated proteins. These mutated proteins, though, are similar if not identical to the proteins of the newly metastasized tumor cells and tumor stem cells. Consequently, these further antibodies are expected to be highly effective against the newly metastasized tumor cells and tumor stem cells.

Furthermore, as a result of the blood filtration system (in certain embodiments) of the system and method, the patient's blood has now been cleansed of the regular circulating tumor cells, tumor stem cells and tumor breakdown products that were in the process of metastasizing. Therefore, when the reprogrammed tumor cells, tumor stem cells and tumor breakdown products is injected into the patient's body, the previous metastasis occurring within the patient's body has been inhibited for this additional reason. Since this cleaning and reprogramming is performed exogenously like kidney dialysis, certain embodiments of the methods herein are called an "oncodialysis method" and certain embodiments of the system can be said to be an "oncodialysis system".

Furthermore, and without being bound or limited by theory, Applicant believes that the reprogramming (for example coagulation) degrades the outer layer of the separated tumor entity by removing at least one external layer (for example at least one external water layer) and in some cases two or three or four or five external layers (for example two or three or four or five external water layers) surrounding the protein of the separated tumor entity (tumor cell, tumor stem cell, tumor breakdown product, exosomes etc.). Without being bound by theory, Applicant also believes that tumor entities that have not been reprogrammed—such as newly created tumor entities that form after reinjection of the reprogrammed tumor entities—naturally have gaps in their outer layers that expose their proteins. Therefore, the autologous antibodies that are created by the body to attack the reprogrammed tumor entities (that may have highly exposed proteins) will also immunologically notice the proteins exposed by the gaps in the outer layer of newly created tumor entities (i.e. the future newly created tumor cells, tumor stem cells and newly created breakdown products that break off from the tumor, metastasize and circulate in the patient's blood after any cleaning of the blood and reinjection of reprogrammed tumor entities).

The process of removing the blood and purifying it of oncological components during a session by isolating the circulating tumor cells, circulating tumor stem cells and their circulating components may be repeated at intervals of about 7 days to about 10 days, for example, 7 days or 8 days or 9 days or 10 days, or another interval. If two hundred cc (cubic centimeters) of blood is removed during each session, it would require about twenty-five sessions to clean all of the blood for the average adult. Shorter intervals (i.e. 6 days) are possible between sessions so long as the particular patient can tolerate the blood removal (and taking into consideration the amount of blood removed in each session and the capacity if the blood filtration system). Longer intervals are also possible but one has to take into consideration how much time the patient can tolerate the tumor (and the amount of blood removed in each session). It is noted that the effectiveness of the vaccine to trigger antibodies in the patient is not dependent on the cleaning of all of the patient's blood. In fact, in some embodiments and depending on the health of the patient, in one or two sessions of isolating the tumor components after each of which the reprogrammed tumor cells, tumor stem cells and tumor breakdown products are injected into the patient, the immune system of the patient already attacks the reprogrammed cell and cell components as well as newly formed tumor cells.

The system and method, in certain embodiments, can also be used to determine if an asymptomatic patient has cancer. This can be used to replace a liquid biopsy. The separated material obtained during the filtration by the blood filtration system 50 is inspected or tested to reveal whether tumors are present. This method avoids the significant pain caused by a biopsy.

Alternatively, instead of taking blood from the patient as the source from which to separate out the tumor cells, tumor stem cells and tumor breakdown products, in some implementations of methods 200, 300, 400 and in some preparations for the utilization of systems 10, 100, fluid samples may be taken from the lymphatic system of the patient at the lymph node location at which the cancer is most likely to first spread. This is done using a lymphatic canulation (inserting a cannula into the lymphatic vessels) or a sentinel lymph node biopsy (SNLB) or dissection. Sentinel lymph nodes are the first lymph node to which the cancer cells are most likely to spread (in the case of breast cancer the sentinel lymph nodes would be axillary lymph nodes (armpit), in the case of lung cancer the sentinel lymph nodes would be thoracic lymph nodes, and so on). Tumor cells situated at the lymph nodes/lymphatic fluid may also be separated or filtered respectively and then reprogrammed later to be reinjected intramuscularly (IM).

In certain embodiments, the rotatable filter of the blood filtration system includes multiple layers each layer having differently-sized apertures to retain differently-sized materials from among (i) tumor cells of different sizes, (ii) tumor stem cells and (iii) tumor breakdown products (such as tumor DNA, tumor protoplasm or other breakdown products of the tumor cells or of the tumor stem cells).

In some embodiments, the system also includes at least one device for directing electromagnetic radiation at the separated out tumor cells, separated out tumor stem cells and separated out tumor breakdown products (which may be one or more of tumor DNA, tumor protoplasm, tumor exosomal proteins and other breakdown products of the tumor cells and tumor stem cells), for example while these separated components or cells are situated in a container that may be in communication with or form part of the filtration system. The electromagnetic radiation coagulates an outer surface of at least one of (i) the separated tumor cells, (ii) the separated tumor stem cells and (iii) the separated tumor breakdown products such as DNA or other protein or breakdown products of the cells (tumor cells or tumor stem cells) so that they (one or more of them) acquire a coagulated outer layer. The electromagnetic radiation may have a UV wavelength. In some embodiments another device of the at least one device has a Terahertz frequency. In some embodiments, ozonated water and/or hydrogenated water is applied during the reprogramming phase. The system may also include a processing unit configured to control the blood filtration system as well as any other hardware and software needed to implemented the steps of the method 200 and the systems 10, 100 outlined herein.

In general, for the systems and methods to be effective, Applicant believes that the mammalian subject has to have an adequate white blood cell count and a functioning bone marrow. One way of testing this is by testing the bone marrow of the subject's femur. This testing can be accomplished in a number of ways, including non-invasively through imaging modalities. If the bone marrow in a patient's femur is 30% of the normal amount, there is an adequate amount for the system and method to succeed. If not, a special tissue suppression therapy is utilized to rehabilitate the subject's bone marrow. Applicant has reason to believe that among patients with at least 30% of their bone marrow, a success rate of 70% will be achieved, wherein success is defined as shrinking the size of the tumor or at least halting tumor growth or metastasis, in either case as defined by the results of a PET-CT. Applicant believes that merely halting metastasis is quite beneficial since according to Applicant, typically the patients do not succumb to the cancer itself directly but rather to an infection after the cancer debilitates the bone marrow as a result of the continuing metastasis thereby harming the body's ability to fight the infection.

In some embodiments, the vaccine comprises a variety of different reprogrammed tumor-derived elements from among: (i) tumor cells, (ii) tumor stem cells, (iii) tumor breakdown products, which tumor breakdown products themselves may be of a variety of different kinds including tumor DNA (and other tumor proteins), tumor protoplasm and tumor exosomal peptides or proteins. In some embodiments, this diversity increases the likelihood of the vaccine triggering the broadest range of antibodies that can then be used against the broadest range of proteins, while at the same time ensuring that the antibodies will be effective since they all autologous and derive from the patient's own reprogrammed tumor entities or elements. As such, the vaccine is personalized to the patient/subject.

The principles and operation of an Oncodialysis System and Method for Personalized Autologous Cancer Vaccine and Blood Purification according to the invention may be better understood with reference to the drawings and the accompanying description.

FIG. 1 shows one embodiment of a system 10 of oncodialysis. Blood containing circulating tumor cells and circulating tumor stem cells are removed from veins of the subject or patient 15, in one particular non-limiting implementation in amounts of about 200 cc at a time or during one therapeutic session. Instead of removing about 200 cc in one session another amount may be removed taking into consideration the patient's ability to endure blood removal and the number of sessions that are suitable for the patient given the patient's health. The amount of blood that can be filtered by the blood filtration system is also taken into consideration. Therefore, in general the number of cc removed may vary from 40-300 (or in other embodiments from 40-200 or from 50-300 or any number in between 40 and 300, or any other suitable quantity). In some embodiments, the removal of the blood from the patient is accomplished by means of a peristaltic pump 20, at a venous output of the patient (for example the veins of one particular arm of the patient).

As seen from FIG. 1, in certain embodiments, a first pump, for example a first peristaltic pump 20 is configured to create a vacuum to draw the blood out of the patient and into the pump (depending on the direction of the moment of the pump, which is controlled) whereas a second pump downstream of the blood filtration system 50 is configured to draw the blood out of the pump. In certain embodiments, since the blood movement generated by the peristaltic pump 20 is in the form pulsations, a damper 30 may be situated downstream of the pump 20 to maintain smooth flow of the blood. The damper 30 may be a conically arranged or shaped coil 30 downstream of the pump 20 configured to maintain smooth flow of the blood, for example by increasing a uniformity of the flow rate of the blood.

In one implementation, coil 30 may be at least one conically arranged or conically shaped coil 30 for maintaining smooth flow of blood upstream of the blood filtration system such as by increasing the uniformity of the flow rate of the blood. The at least one conically arranged or conically shaped coil 30 may include at least one coil 30 configured to maintain smooth flow of blood downstream of the blood filtration system (such as by increasing the uniformity of the flow rate). In some embodiments, system 10 comprises at least one conically arranged or conically shaped coil 30 comprising a first coil 32 upstream of an inlet of the blood filtration system and a second coil 34 downstream from an outlet of the blood filtration system 50. The coils 32, 34 also prevent hemolysis. This is the destruction of the red blood cells, which although normal, would interfere with the cleaning or filtering of the blood by the blood filtration system 50. Since the coils slow the blood flow rate, especially at the base of the coil (which is wider) there is less turbulence or tension during the blood flow that would normally induce hemolysis.

The blood may continue into a blood reservoir 40 from which it travels through an inlet (not shown) of a blood filtration system 50 into the blood filtration system 50.

System 10 may include a blood filtration system 50 for filtering exogenous blood plasma to separate at least one of (i) tumor cells, (ii) tumor stem cells and (iii) tumor breakdown products (which tumor breakdown products may include one or more of tumor protein such as tumor DNA, tumor exosomal peptides, tumor protoplasm and other tumor breakdown products. The blood filtration system 50 may comprise a filter 52 that may have multiple layers, each layer having differently sized apertures so as to retain differently sized materials from among (i) the tumor cells of different sizes, (ii) the tumor stem cells and (iii) the tumor breakdown products. Note that the (i) tumor cells, (ii) tumor stem cells and (iii) tumor breakdown products were circulating in the blood of the patient when the removed blood was previously circulating in the subject's/patient's body.

In some embodiments, the blood filtration system 50 may also include a filter 52. System 50 may be configured to first filter the exogenous blood of the subject in order to separate out the exogenous blood plasma prior to a step of filtering the exogenous blood plasma to separate the tumor cells, tumor stem cells and/or tumor breakdown products.

Figure 3A:
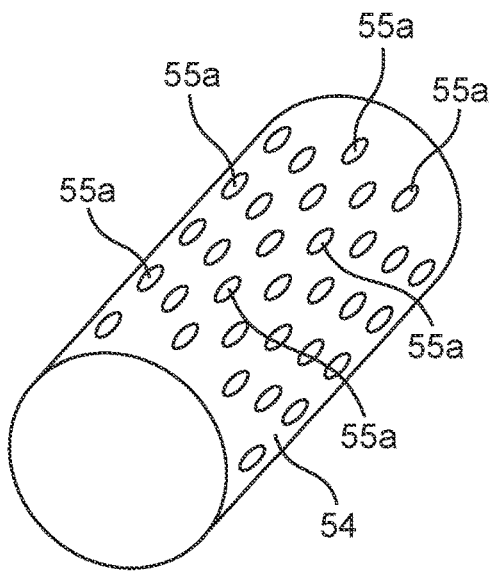
FIG. 3A is a view of the outer layer of a multilayer filter of a blood filtration system, in accordance with one embodiment.
Figure 3B:
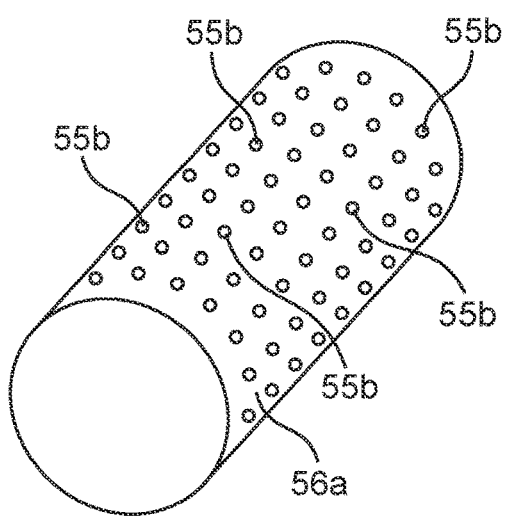
FIG. 3B is a view of an outermost intermediate layer of a multilayer filter of a blood filtration system, in accordance with one embodiment.
Figure 3C:
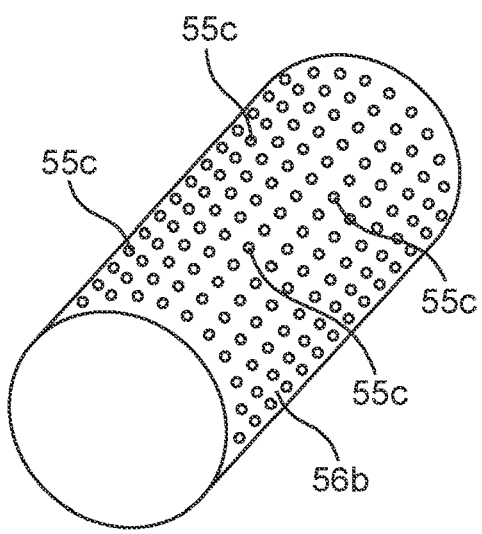
FIG. 3C is a view of another intermediate layer of a multilayer filter of a blood filtration system, in accordance with one embodiment.
Figure 3D:
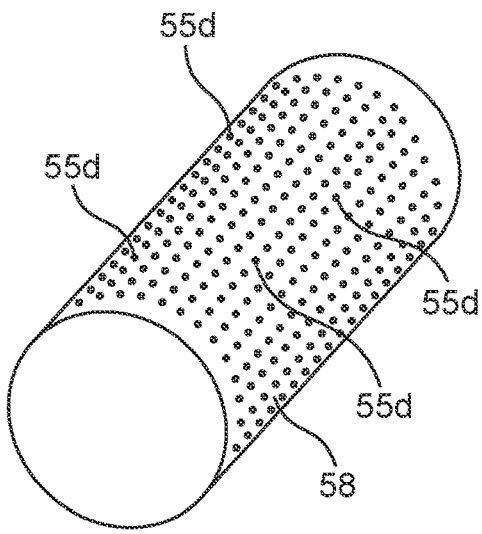
FIG. 3D is a view of the inner layer of a multilayer filter of a blood filtration system, in accordance with one embodiment.

The blood filtration system 50 may comprise a filter 52 that includes one or more layers. In one version, filter 52 is a multilayer filter 52. The filter 52 or multilayer filter 52 may be a rotatable filter 52. In the case of a multilayer filter, the multilayer filter 52 may include an outer layer 54 (FIG. 3A) configured to retain the tumor cells. Filter 52 or multilayer filter 52 may have apertures 55a of a first diameter. One or more intermediate layers 56 of multilayer filter 52 may include a second outermost layer 56a configured to retain the tumor stem cells and having apertures 55b of a second diameter smaller than the first diameter. In some embodiments, the multilayer filter 52 further comprises an inner layer 58 configured to retain the tumor DNA and having apertures 55d of a third diameter smaller than the second diameter.

In some embodiments, the multiple layers of the rotatable filter 52 include an outermost layer 54 having apertures 55a configured to retain tumor cells of a largest size, an outermost intermediate layer 56a having apertures 55b configured to retain tumor cells of a next largest size, another intermediate layer 56b having apertures 55c configured to retain tumor stem cells and an additional intermediate layer 56c having apertures 55d configured to retain tumor breakdown products (such as tumor DNA or tumor protoplasm) of the tumor cells or stem cells. There could also be five layers (54, 56a, 56b, 56c, 58) having differently sized apertures or more than five. For example there could be multiple layers having diameters of descending size for retaining differently sized tumor cells and then one or more layers having apertures of smaller diameter (of descending size) for stem cells and one or more layers for tumor DNA or other breakdown products (of the tumor cells or tumor stem cells) having still smaller diameters. There could also be just two layers.

Blood filtration system 50 may also include a base 51, in one non-limiting example a substantially rectangular base 51, that supports the multilayer filter 52. Any such base 51 may also support or house an actuator 53 configured to rotate the filter 52 forward and backward through a defined rotational sector, for example through a rotational sector of about 45 degrees (or through a rotational sector of between 30 and 60 rotational degrees), as denoted by the dashed arrows in FIG. 1. In one non-limiting implementation, the actuator 53 comprises one or more motors.

As the filter 52 rotates back and forth, the forces on the tumor cells, stem cells, tumor DNA cause these elements to be filtered through the various layers (sometimes called floors) of the filter 52. For example, the tumor cells, stem cells and tumor DNA may filter through (i.e. traverse) between zero and one or two or three or four or more layers (sometimes referred to as floors) of the filter 52 by traversing the apertures 55 or not traversing the apertures 55 of the walls of each layer or floor, depending on their size and the size of the apertures 55. In some embodiments, the apertures 55 of filter 52 are smaller and smaller as one moves from the outer layer of filter 52 toward the inner layer 58 of filter 52, as seen from FIG. 3A, FIG. 3B, FIG. 3C and FIG. 3D.

As seen from FIG. 1, in accordance with certain embodiments, after being separated out by the blood filtration system 50, the tumor cells, the tumor stem cells and tumor breakdown products such as tumor protein may be subjected to electromagnetic radiation by at least one device 70 (see FIG. 1 and FIG. 2) configured to direct electromagnetic radiation at them. The electromagnetic radiation may be at a UV wavelength (for example 100-400 nm). For example, the at least one device 70 may comprise two or more devices and the UV radiation may include at least two of the following types of UV radiation: (i) UVA radiation (315-400 nm), (ii) UVB radiation (280-315 nm) and (iii) UVC radiation (100-280 nm). In some embodiments, the electromagnetic radiation used is UVC wavelength or in other embodiments one or more of (i) UVC wavelength radiation and (ii) UVB wavelength radiation is applied. In some embodiments, the electromagnetic radiation applied is from 100 nm to 300 nm (visible light being from about 300-400 nm) or in certain embodiments from about 100 to about 300 nm. In certain embodiments, if two or three of UVA, UVB and UVC radiation is applied, then each of the UVA, UVB and UVC radiation may be provided separately such as by using separate devices 70 (i.e., two or more devices) or in other embodiments by a single device 70. In one particular embodiment, only UVC radiation is applied. In the case of tumor exosomes, in one embodiment UVC radiation is applied. In some embodiments, UVC radiation of about 100 nm is applied, for example about 100-110 nm or 90-110 nm or 100-120 nm or 90-120 nm or 100-130 nm or 90-130 nm or about 100-140 nm or about 100-150 nm.

Without being bound by theory, Applicant has found that UVA and UVB strengthens the effect of UVC radiation. Furthermore, UVA and UVB are weaker than UVC. Accordingly, while UVA and UVB coagulate the outer envelope of the tumor cells, tumor stem cells, UVC causes coagulation of not only the outer envelope of the tumor cells and tumor stem cells but also their nuclei. In fact, in many cases, UVC kills the tumor cells and tumor stem cells. These dead cells are effective (once reinserted into the subject's body) at triggering autologous antibody production by the subject's immune system. In general, it is helpful to use UVA, UVB and UVC radiation in order to maximize the effects since different tumor cells or tumor stem cells require different frequencies of electromagnetic radiation 720 in order to have their outer envelope coagulated.

Accordingly, in one implementation, UVA radiation, UVB radiation and UVC radiation 720 are each directed to the one or more of (or in other embodiments two or more of or in other embodiments three or more of) the separated tumor cells, separated tumor stem cells and separated tumor breakdown products (of the tumor cells or stem cells, which may include tumor DNA or other tumor protein, tumor exosomes (such as tumor exosomal peptides), tumor protoplasm or other tumor breakdown products) by at least one device 70 which may be at least one radiation device 70. This may be performed by different devices 70 (i.e. different radiation devices 70) for each type of radiation and this may be performed one after the other (i.e. not at the same time). In one version, UVA radiation is first applied by one device 70 for 5-9 seconds, then UVB radiation is applied by a second device 70 for 5-9 seconds, then UVC radiation is applied by a third device for 5-9 seconds. In another implementation, one of UVA radiation or UVB radiation is applied and UVC radiation is also applied (in one implementation of this for example UVA is applied followed by UVC or UVB is applied followed by UVC). In some embodiments, only one type of radiation is applied.

In one implementation, UV radiation 720 is directed at one or more of (or in other embodiments two or more of or in other embodiments three or more of) the separated tumor cells, separated tumor stem cells and separated tumor breakdown products of the tumor cells or stem cells continuously for a period of about 5 to about 9 seconds (or for some amount of time greater than about 5 seconds and less than about 9 seconds) for each type of electromagnetic radiation 720 that is applied.

In some embodiments, the at least one device 70 further includes a device 72 for directing electromagnetic radiation 720 at one or more of (in other embodiments at least two or in other embodiments all three of) the separated tumor cells 91, separated tumor stem cells 92 and separated tumor breakdown products (including for example tumor DNA 93) or other breakdown products to produce the coagulated outer layer 91a, 92a, 93a, the electromagnetic radiation 720 having a terahertz frequency of up to about 0.1 terahertz (at least about 2,997,924.58 nm or in other embodiments at least about 3 million nm).

In any embodiment described herein, the electromagnetic radiation 720 (for example UVC or any other electromagnetic radiation 720) directed by the at least one device 70 may cause an outer layer of the separated tumor entity (tumor cell, tumor stem cell and/or tumor breakdown product) to degrade so as to expose proteins beneath such outer layer.

One embodiment of system 10 is a system for preparing a cancer vaccine for a mammalian subject having a circulating tumor entity, wherein the system 10 may comprise a blood filtration system 50 for filtering exogenous blood plasma to separate out an oncological component (for example from the blood plasma), the oncological component comprising at least one of (i) tumor cells, (ii) tumor stem cells and (iii) tumor breakdown products, the oncological component not configured to be recognized as an antigen by an immune system of the subject. The oncological component made be made up primarily of the at least one of (i) tumor cells, (ii) tumor stem cells and (iii) tumor breakdown products and may have a remnant of blood plasma comprising in some embodiments less than about 5% by volume or less than about 1% by volume or in some embodiments less than about 0.5% by volume or in some embodiments less than about 0.1% by volume of the oncological component.

The system 10 may also comprise at least one device 70 for directing electromagnetic radiation 720 at the separated oncological component so as to convert an outer surface of the at least one of the (i) separated tumor cells, (ii) separated tumor stem cells and (iii) separated tumor breakdown products into a coagulated outer layer and thereby convert the oncological component to something that the immune system of the subject will recognize as an antigen when reinserted into the subject's body (for example when reinserted or reinjected into the subject's bloodstream after being reprogrammed for example by having its outer surface coagulated or degraded or altered). The electromagnetic radiation may have a UV wavelength. One example of converting the oncological component into something that will be recognized by the immune system as an antigen is by degrading the outer layer of the separated tumor entity, for example by degrading the outer layer of water of the separated tumor entity, which degrading may cause coagulation of the outer layer of the separated tumor entity.

The system 10 may also comprise a processing unit 80 configured to control the blood filtration system 50. Processing unit 80 may include one or more processors 82 that execute programming instructions 84 such as software 84 that is stored on memory 86. System 10 may also include any other hardware of software needed to implement the system.

In some embodiments, the blood filtration system 50 is configured to separate out from the exogenous blood plasma a yield of the oncological component (which may then be subjected to reprogramming). The yield of the oncological component may still contain only a remnant of the blood plasma, such as a negligible remnant of blood plasma. In some embodiments, the negligible remnant of the blood plasma in the separated oncological component is less than about 5% by volume, and in some embodiments, less than about 1% by volume, and in some embodiments, less than about 0.5% by volume, and in some embodiments, less than about 0.1% by volume and in some embodiments another percentage (or less than another percentage) in between 1% and 5% or in between 0.5% and 1% or in between 0.1% and 0.5%. Accordingly when reprogramming the separated out oncological component using electromagnetic radiation 720 to for example degrade an outer layer of the tumor entities and generate a coagulated outer layer, an advantage is achieved in some embodiments in that cancerous proteins rather than healthy proteins are irradiated. Consequently, when the reprogrammed tumor entities are reinserted or reinjected into the subject's body, the antibodies triggered by the immune system of the subject are configured for tumor entities and not for healthy protein. This minimizes autoimmune diseases from the antibodies.

Additionally, in some embodiments, the system 10 has the advantage of separating out multiple types of oncological components (rather than just a single type) such that when reprogramming and reinsertion into the body occurs, the system 10 is configured to trigger an attack by the immune system of the subject on multiple and varied tumor entities that had been separated out. Thus, the attack of the immune system by autologous antibodies on the reprogrammed tumor entities is more varied and thorough than in prior art systems. For example, the oncological component may comprise at least two of or in other cases all three of (i) tumor cells, (ii) tumor stem cells and (iii) tumor breakdown products. Furthermore, in some embodiments, the separated out oncological component may comprise tumor breakdown products that may include tumor exosomes (in which case the blood filtration system may also include a centrifuge) and/or DNA. In certain embodiments of system 10, as part of the reprogramming, the system 10 further includes a device 71 (FIG. 5) configured to provide ozonated water which is applied to (an outer surface of) the isolated tumor cells, isolated tumor stem cells and isolated tumor DNA or other tumor breakdown products, preferably after application of the UV radiation, for example UVC (and/or UVA and/or UVB). The ozonated water may have a concentration of about 5 mcg per ml to about 15 mcg per ml of solution. The ozonated water, if used, serves to further ensure that the coagulation occurs.

In certain embodiments, whether after application of the ozonated water or prior to or even without regard to application of ozonated water, system 10 includes a device 72 (FIG. 5) configured to apply hydrogenated water to an outer surface of the isolated tumor cells, isolated tumor stem cells and isolated tumor breakdown products. In some embodiments, the hydrogenated water has a pH of 8-10 and has an oxidation-reduction potential of from −400 mV to −800 mV. As a result, the hydrogenated water creates an alkaline environment so as to kill circulating tumor cells and tumor stem cells and tumor breakdown products, albeit retaining the basic form of the cells. Dead tumor cells (as opposed to live tumor cells) are more likely to be recognized as antigens by the body.

The same is true of frozen tumor cells and frozen tumor breakdown products—they are more likely (as opposed to tumor cells and tumor breakdown products that have not been frozen) to be recognized by the patient's immune system as antigens. In some embodiments, one or more of the reprogrammed tumor cells, reprogrammed tumor stem cells and reprogrammed tumor breakdown products (i.e. DNA) are frozen (prior to being injected into the subject). The length of the freezing time, in certain embodiments, is an amount of time sufficient to cause crystallization of the one or more of the tumor cells, tumor stem cells and tumor breakdown products. For example the freezing time may be about 5-13 minutes or in some embodiments for about 8 minutes to about 10 minutes (or another length of time configured to cause crystallization). In some embodiments, the freezing occurs by setting the temperature of a container in which the tumor cells and breakdown products are placed to a temperature somewhere from about minus 5 degrees to about minus 10 degrees Celsius. The freezing is performed prior to injecting the reprogrammed cells/components to the patient. This freezing causes crystallization of the tumor cells, tumor stem cells and tumor breakdown products (such as peptides) so as to increase the likelihood that the subject's immune system will recognize these cells or components as antigens.

Figure 5:
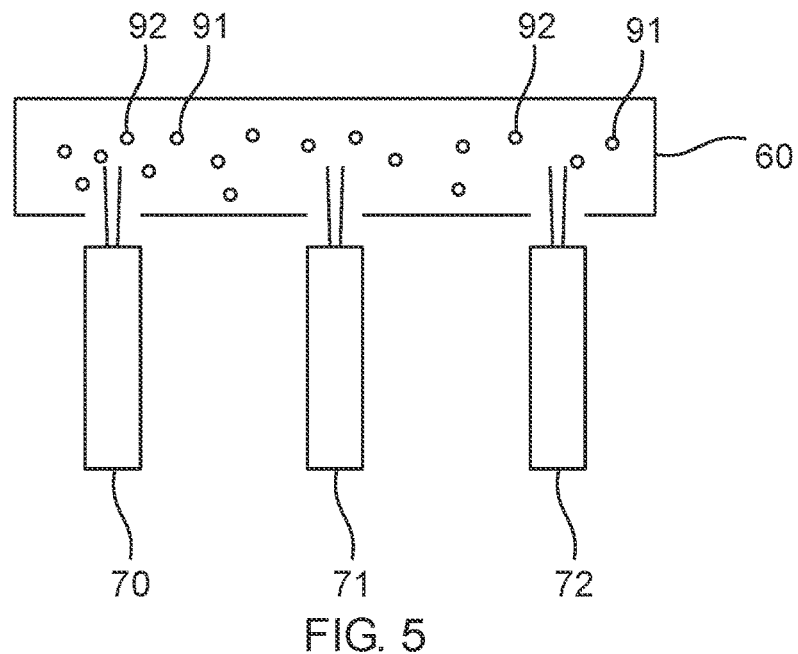
FIG. 5 is a schematic illustration of various devices being used in reprogramming the tumor cells, tumor stem cells and breakdown products of the tumor cells and tumor stem cells.

As illustrated in FIG. 5, the reprogramming of at least one of the tumor cells, tumor stem cells and tumor breakdown products (such as DNA or other breakdown products) may occur while the tumor cells or tumor stem cells or tumor breakdown products are in a container 60, although this is not a requirement.

At least one of reprogrammed tumor cells, reprogrammed tumor stem cells and reprogrammed tumor breakdown products may then be (after the process or processes of reprogramming) injected into a muscle of the patient 15 for example at the buttocks (or delivered inside the subject's/patient's body in some other way), in accordance with some embodiments. In addition, the cleaned or purified blood (after passing, in accordance with certain embodiments, through a further peristaltic pump 20 and a further conically arranged coil 30) is recirculated in some embodiments by means of further tubing 29 into the subject's/patient's veins (typically the vein of the patient's other arm rather than the veins of the arm from which the blood was drawn).

Accordingly, the electromagnetic radiation 720 (and in some versions also one or more of the ozonated water, the hydrogenated water and the freezing (for example for about 5 or 6 or 7 or 8 minutes to about 10 or about 11 or about 12 or about 13 minutes (for example 8-10 minutes)) causes the outer layer of each of the isolated components (tumor cells 91, tumor stem cells 92 and tumor cell breakdown products 93 such as tumor DNA 93) that it is applied to, to coagulate or form a coagulated outer layer 91a, 92a, 93a, thus in effect undergoing a "reprogramming" that renders these components antigens that when injected into the subject/patient trigger autologous antibody production by the patient's immune system. In some embodiments, because the injection into the subject of the vaccine described herein occurs soon (within hours) after the reprogramming, it is unnecessary to utilize preservatives as part of the vaccine.

Furthermore, the blood itself that is then recirculated into the patient is purified blood that has been cleansed of (for example cleansed of most of in some embodiments) the circulating (metastasizing) tumor cells and circulating tumor stem cells and their respective breakdown products (i.e. DNA and other tumor breakdown products) by the blood filtration system 50.

System 10 may also include a processing unit 80 configured to control the blood filtration system 50. Processing unit 80 may include one or more processors 82 that execute programming instructions 84 such as software 84 that is stored on memory 86. System 10, 100 may also include any other hardware of software needed to implement the system (or any method 200 described herein). Processors 82 may control the frequency at which the actuator 53 or another component rotates the filter 52 forward and backward through the defined rotational sector. If the yield of the tumor cells, tumor stem cells or tumor breakdown products (after inspection) is not high enough to meet a predefined criteria, the processor 82 may change the frequency and the magnitude of the sector (rotational angle) through which the rotation occurs. In some embodiments, artificial intelligence, such as machine learning, is used by the processor(s) 82 to perform these functions, including controlling the frequency of the rotation of the filter 52, controlling the magnitude of the sector through which the rotation occurs (i.e. the rotational angle) and determining whether the yield of the filter 52 meets the desired predefined threshold amount of tumor cells, tumor stem cells and/or tumor breakdown products.

Figure 4:
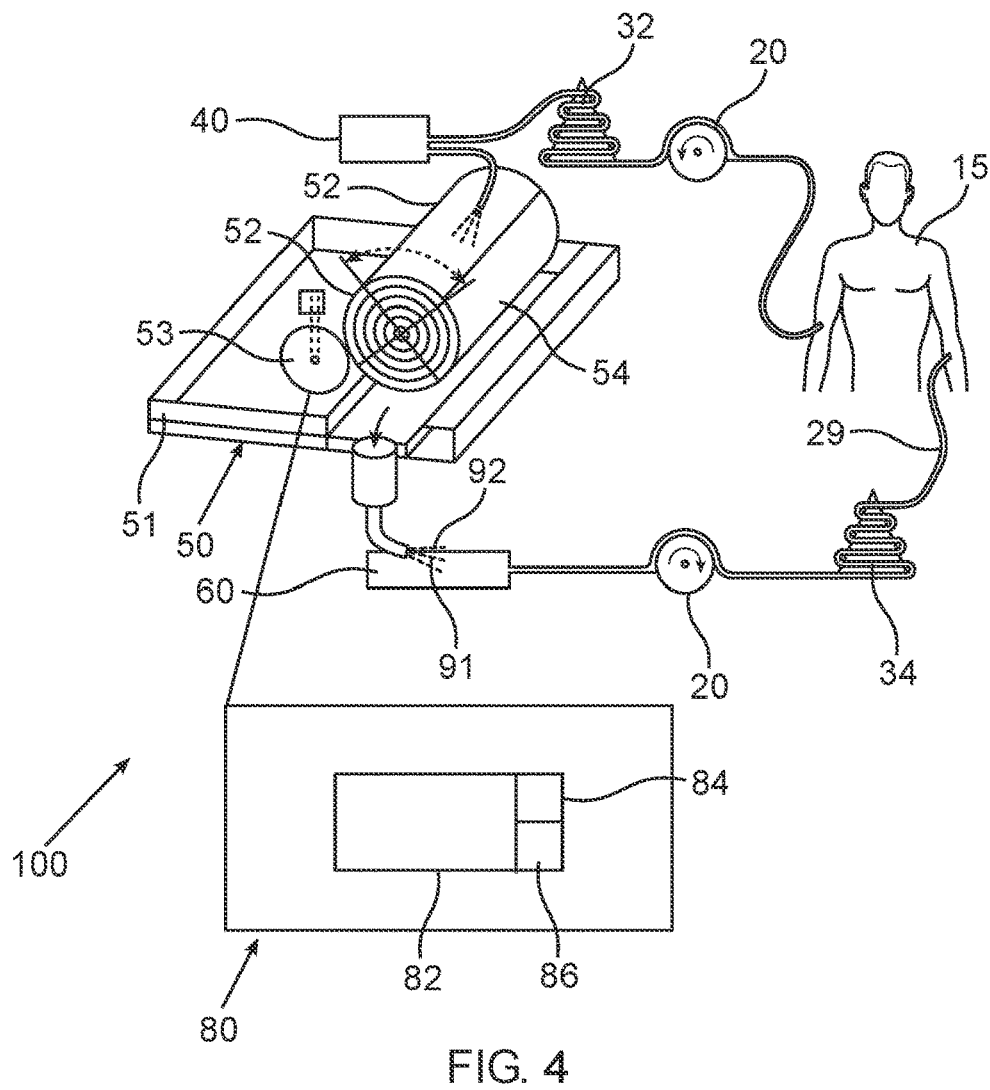
FIG. 4 is a schematic illustration of another version of a system, in accordance with one embodiment.

In another embodiment, as shown in FIG. 4, system 100 does not include the at least one device 70. System 100 may include the at least one coil 30 (such as coils 32, 34). For example, system 100 may comprise a system 100 for cleaning blood of a mammalian subject having a cancerous tumor, comprising a blood filtration system 50 for filtering exogenous blood. The filtration system 50 may filter plasma from a remainder of the exogenous blood. In some embodiments, the filtration system 50 of system 100 is configured to start off with exogenous blood plasma as the input. In that case, filtration system 50 is configured to filter and thereby isolate at least one of (or in some other embodiments at least two of or in some other embodiments all three of) (previously circulating) tumor cells, (previously circulating) tumor stem cells and (previously circulating) tumor breakdown products such as DNA from the exogenous blood plasma of the subject.

The blood filtration system 50 may include a rotatable filter 52 having multiple layers.

As seen from FIG. 4, system 100 may include at least one conically arranged or conically shaped coil 30 comprising a first coil upstream of an inlet of the blood filtration system and a second coil 30 downstream from an outlet of the blood filtration system 50. System 100 may also include a processing unit 80 (in any version described with respect to system 10 including machine learning and artificial intelligence) configured to control the blood filtration system 50.

Any version of the elements (other than device 70) of system 10 may be used in the respective elements of system 100. For example, any version of the blood filtration system 50 (or its layers) or coil 30 described with respect to system 10 may be used in the blood filtration system 50 or coil(s) 30 of system 100. Similarly, there may be a pump 20 in system 100 just as there may be in system 10.

In certain embodiments, system 10 or system 100 may also include a centrifuge 57 (FIG. 3E), which is useful for separating out tumor exosomes 94. This is important because exosomes of even healthy cells are programmed to eventually exit the cell. When tumor exosomes 94 exit tumor cells or tumor stem cells, this constitutes (or causes) metastasis. Furthermore, without being bound or limited by theory the exit of tumor exosomes 94 from tumor cells or tumor cells may occur even before the primary growth (the tumor cell or the tumor stem cell) metastasizes because exosomes exit even healthy cells at an earlier stage than cell apoptosis.

Applicant believes that detection of tumor exosomes 94 or tumor exosomal peptides 94 in the blood by filtration and removal of the tumor exosomes 94, reprogramming of the tumor exosomes 94 (for example by subjecting the outer surface of the tumor exosomes 94 to electromagnetic radiation, for example to cause the outer surface to become coagulated), and reinjecting the reprogrammed tumor exosomes into the body of the patient provides critical advantages. Since the exiting of the tumor exosomes 94 occurs prior to clinical symptoms, in some embodiments, the vaccine based on injecting the reprogrammed tumor exosomes into the patient can stimulate autologous antibodies against the tumor at the earliest possible stage of metastasis, which in some embodiments is before clinical symptoms develop. Furthermore, since the tumor exosomes (and in general exosomes) contain the RNA and DNA of the cells they exit from, in some embodiments, the vaccine developed from the reprogrammed tumor exosomes will be effective to stimulate autologous antibodies that attack the entire tumor. Furthermore, the mere purification of the blood from tumor exosomes 94—even without the reinjection of the coagulated tumor exosomes after its reprogramming—is also important because Applicant believes that exosomes (including tumor exosomes) are able to penetrate the blood-brain barrier because of their tiny size (about 50-80 nanometers) and thereby wreak havoc (e.g. metastasis) inside the brain, which is clearly dangerous.

Figure 3E:
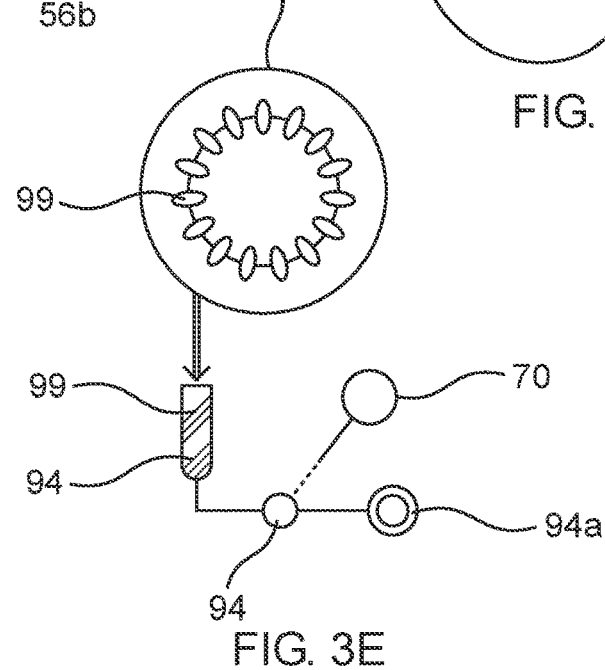
FIG. 3E is a schematic view of a centrifuge of a blood filtration system by which the exosomal fraction is separated from the blood plasma and reprogrammed using electromagnetic radiation, in accordance with one embodiment.

FIG. 3E shows centrifuge 57 of blood filtration system 50 by which the tumor exosomal fraction is separated from the blood plasma 99 and reprogrammed by at least one device 70 using electromagnetic radiation. Accordingly, in some embodiments of system 10, as shown in FIG. 3E, the system 10 includes a centrifuge 57 and in particular the blood filtration system 50 may include a centrifuge 57 configured to separate out tumor exosomes 94 from blood plasma 9, for example by separating tumor exosomes 94 from the blood plasma 99 in a step by step centrifuging process. In some embodiments, the centrifuge 57 is used to do this after the previous purifying of the blood plasma of the tumor cells 91, the tumor stem cells 92 and the tumor breakdown products 93 in general. Since the tumor exosomes 94 are smaller than the other tumor breakdown products, the tumor exosomes will not have been separated out in the previous step of purifying the blood plasma.

The step by step centrifuging process using centrifuge 57 may comprise using a centrifuge 57 at a first speed (for example at an rpm of for example about 1000 (for example 750-1250 rpm), then using the centrifuge 57 (or in theory a different centrifuge) at a second speed (for example 5,000 rpm or 4,000-6,000 rpm for example) and then using the centrifuge 57 (or a different centrifuge) at a third speed (for example 7,000 rpm or for example 6,000-8,000 rpm) to finally obtain the tumor exosomal fraction 94 (FIG. 3E), since the tumor exosomes may weigh the least among the separable components of the centrifuged blood plasma 99. The tumor exosomes 94 are then available to be reprogrammed by applying electromagnetic radiation to the outer layer of the tumor exosomes 94 using the at least one device 70 (for example using UVC).

In some cases, instead of using "rpm" as the relevant centrifuge unit "G" is used. In that case, the relative centrifugal force is set at G in the first step, G+x in the second step and G+y in the third step, where y exceeds x.

In some embodiments, the length of time of use of the centrifuging using centrifuge 57 at the first speed is about 1 minute, the length of time at the second speed is about 1 minute and the length of time at the third speed is about 3-5 minutes. These time periods are just examples and are not limiting.

Furthermore, as shown in FIG. 3E, the at least one device 70 may be configured, in some embodiments, to direct electromagnetic radiation 720 (for example UVC radiation) at the separated (isolated) tumor exosomes 94 to produce the coagulated outer layer 94a of the tumor exosomes 94. Although tumor exosomes are a type of tumor breakdown products 93, tumor exosomes that have been separated out using a centrifuge 57 have been assigned a distinct reference numeral "94" since the separation of such tumor exosomes 94 occurs by a distinct process using this centrifuge 57.

Figure 6:
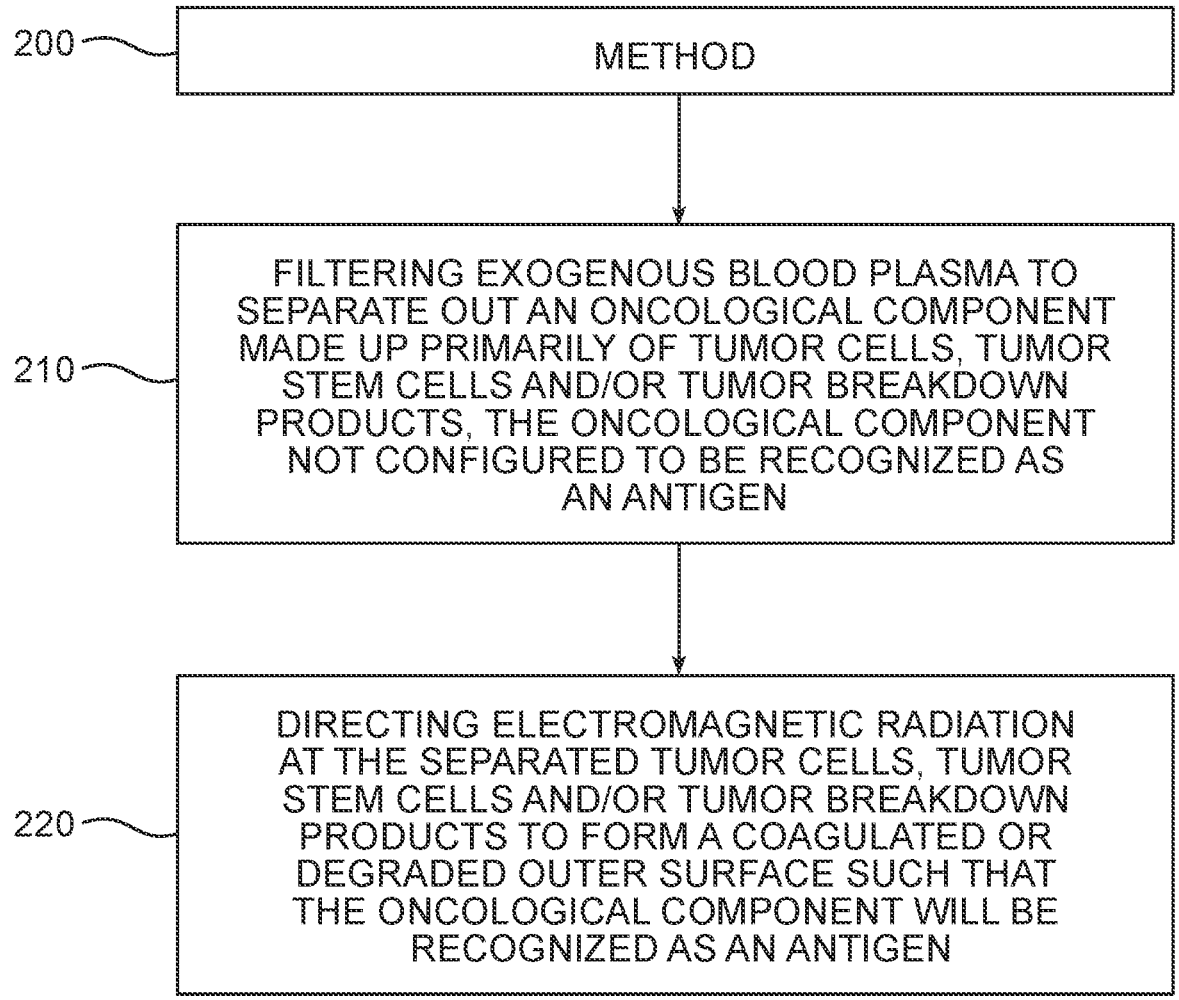
FIG. 6 is a flow chart showing a method in accordance with one embodiment.

As shown in FIG. 6, another embodiment is a method 200 of cleaning exogenous blood and preparing a vaccine against cancer for a mammalian subject using components of the exogenous blood. Method 200 may comprise a step 210 of filtering exogenous blood plasma to separate out an oncological component that is primarily made up of one or more of tumor cells, tumor stem cells and tumor breakdown products, wherein such tumor breakdown products may include one or more of tumor DNA, tumor proteins or tumor peptides or tumor exosomes or tumor exosomal peptides, wherein the oncological component is not configured to be recognized as an antigen by an immune system of the subject.

The separated out oncological component may be made up primarily of the at least one of (i) tumor cells, (ii) tumor stem cells and (iii) tumor breakdown products. The separated out oncological component may have only a remnant of blood plasma comprising in some embodiments less than about 5% by volume or less than about 1% by volume or in some embodiments less than about 0.5% by volume or in some embodiments less than about 0.1% by volume of the oncological component.

In some versions, one first separates the mature circulating tumor cells and then the tumor stem cells. In some versions of method 200, method 200 only includes the step of filtering the patient's blood plasma to separate out one or more of tumor cells, tumor stem cells and tumor breakdown products such as DNA and filtering the exogenous blood to obtain the blood plasma is not part of the method 200.

Method 200 may also include a step 220 of directing electromagnetic radiation at one or more of: (i) the isolated tumor cells, (ii) isolated tumor stem cells and (iii) the isolated tumor breakdown products (such as DNA or tumor exosomal peptides or proteins) so that they acquire a coagulated outer surface or layer 91a, 92a, 93a respectively, and thereby convert the oncological component into something that the immune system of the subject will recognize as an antigen when reinserted (after the oncological component is reprogrammed) into the subject's body.

Figure 2:
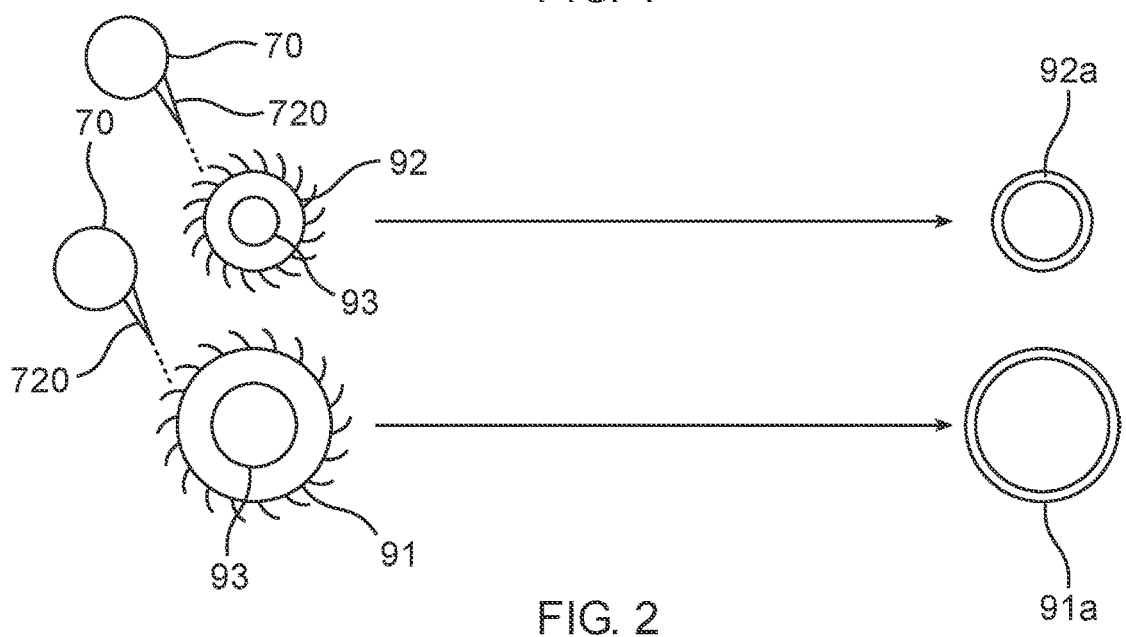
FIG. 2 is a schematic view showing the effect of the electromagnetic radiation on the outer layer of the separated tumor cells, separated tumor stem cells and separated tumor breakdown products, such as DNA, used in a system and method, in accordance with one embodiment.

In some embodiments, the directed electromagnetic radiation 720 causes coagulation of the outer layer such as by degrading the outer layer of the separated tumor entity (i.e. (i) the isolated tumor cells, (ii) the isolated tumor stem cells and/or (iii) the isolated tumor breakdown products which may comprise DNA and/or tumor exosomes or tumor exosomal peptides). The degrading may occur by removing at least one external layer (for example at least one external water layer) and in some cases two or three or four or five external layers (for example two or three or four or five external water layers) surrounding the protein of the separated tumor entity (tumor cell, tumor stem cell, tumor breakdown product, DNA, exosomes etc.). The depiction of tumor breakdown products 93 in FIG. 2 is merely one non-limiting example.

In some embodiments, the electromagnetic radiation 720 directed at the tumor entity has wavelengths in the UV range. In some embodiments, the UV radiation is UVC radiation. In some embodiments, the UV radiation is UVC radiation and one of UVA or UVB radiation. In one non-limiting version, the UV radiation comprises at least two of UVA radiation, UVB radiation and UVC radiation, the UVA, UVB and UVC radiation provided separately. In some embodiments, the UV radiation comprises UVA radiation, UVB radiation and UVC radiation, each applied separately. As with system 10, in step 220 of method 200, the electromagnetic radiation 720 may be directed for about 5 seconds to about 9 seconds (for each type of radiation (UVA, UVB, UVC)) or anything in between. Applying the electromagnetic radiation—particular UVC radiation—for longer than 9 seconds runs the risk of causing undesired mutations.

In certain embodiments, method step 220 includes directing the electromagnetic radiation using a device 70 (any version of device 70 described with respect to system 10) configured for irradiating the tumor cells, tumor stem cells and DNA (or other breakdown products of the tumor cells) with electromagnetic radiation of up to 0.1 terahertz.

Method 200 may also include a step of using a processing unit 80 to control the filtering of the blood plasma, for example by controlling a blood filtration system 50 that implements the filtering of the blood plasma.

In certain embodiments of method 200, step 220 further includes applying ozonated water to the isolated tumor cells, isolated tumor stem cells and isolated DNA or other breakdown products of the tumor cells. The ozonated water may have a concentration of about 5 to about 15 mcg per ml of solution. Method 220 may also include applying hydrogenated water to the at least one of the isolated tumor cells, isolated tumor stem cells and isolated tumor breakdown products to create an alkaline environment. For example, the hydrogenated water may have a pH of about 8 to about 10 and an oxidation-reduction potential of about −400 to −800 mV. Step 220 may also include, in some embodiments, freezing the one or more of the reprogrammed tumor cells, reprogrammed tumor stem cells and reprogrammed tumor breakdown products prior to being injected into the subject, for example for about 5-13 minutes or in some embodiments for about 8 to about 10 minutes prior to giving it to the patient to cause their crystallization thereby increasing the likelihood that the subject's the body will recognize them as antigens.

Method 200 may include a further optional step of injecting the irradiated DNA, previously circulating tumor cells and tumor stem cells into the patient to induce the patient's immune system to produce autologous antibodies against the coagulated outer surface.

In step 210 of method 200 (and in general in any of the other methods 300, 400) any version of filtration system 50 and of filter 52 may be used that has been described with respect to system 10 or system 100.

As one non-limiting example, method step 220 may include filtering blood plasma of the patient using a blood filtration system 50 that includes a filter, such as multilayer filter, which may be a rotatable filter. Each layer of the multilayer filter may be configured for differently-sized tumor cells or tumor cell breakdown products. Likewise, method step 210 may include using a rotatable filter that has an outer layer configured to retain the tumor cells and having apertures of a first diameter and a second layer configured to retain the tumor stem cells and having apertures of a second diameter smaller than the first diameter. In some versions, the rotatable filter further comprises an inner layer configured to retain the tumor DNA and having apertures of a third diameter smaller than the second diameter. Method step 210 may include utilizing a rotatable filter that includes an outermost layer having apertures configured to retain tumor cells of a largest size, a less outermost layer having apertures configured to retain tumor cells of a next largest size, an intermediate layer having apertures configured to retain tumor stem cells and an additional layer having apertures configured to retain tumor DNA.

Method step 210 may include subjecting the filtered material—for example tumor cells or tumor stem cells or tumor breakdown products—to an oncological evaluation to determine if they are tumor cells or not. Such an evaluation procedure may include staining the cells (or a sample thereof) that were too large to traverse a particular layer of the filter (for example cells that were retained by the outer layer 54 since they were too large to traverse apertures 55*a*) and then looking at these cells under a microscope to determine if they are indeed cancerous. This may be quantitatively compared to the amount of the one or more of the tumor cells, tumor stem cells and tumor breakdown products that existed prior to the filtration of method step 210, which prior amount may have been assessed in an additional substep of method step 210.

Method 200 may include situating at least one conically arranged or conically shaped coil upstream of an inlet of the blood filtration system, and optionally, situating at least one conically arranged or shaped coil downstream from an outlet of the blood filtration system. Each of these is to improve the uniformity of the blood flow rate and to prevent hemolysis, which inhibits cleaning of the blood.

Figure 7:
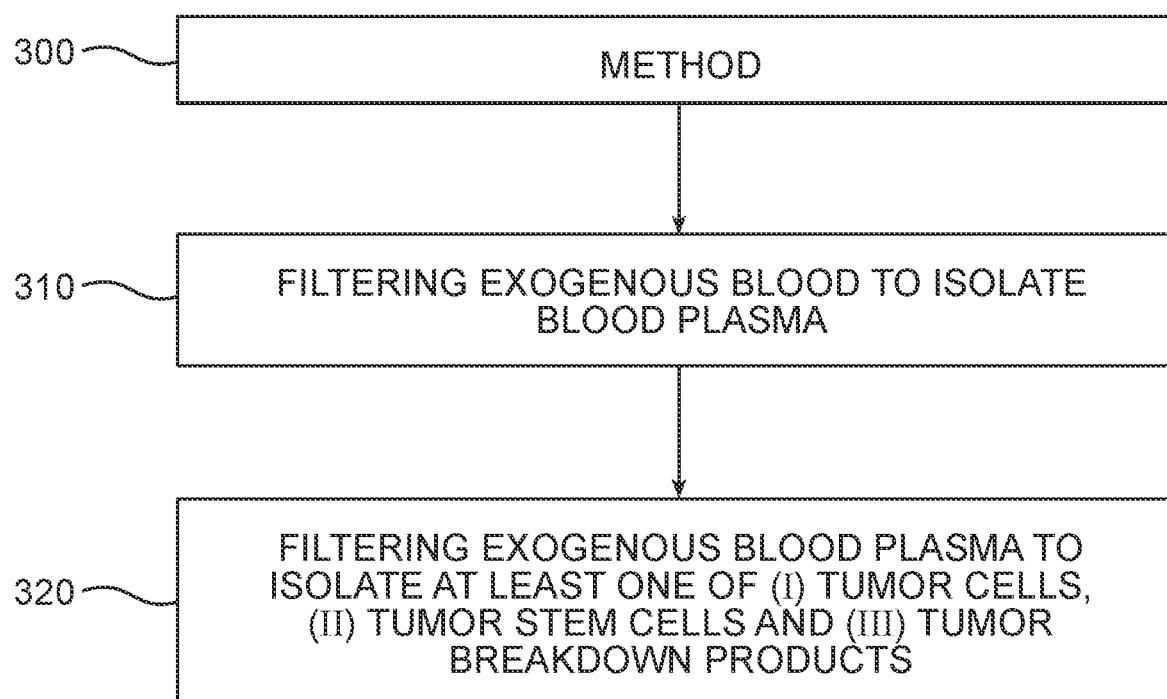
FIG. 7 is a flow chart showing another method, in accordance with one embodiment.

As shown by the flow chart of FIG. 7, one embodiment of method 300 is a method of cleaning blood of a mammalian subject who has a cancerous tumor, wherein the blood has circulating tumor cells, tumor stem cells and/or tumor breakdown products. It is similar to method 200 except omits a step of reprogramming one or more of the separated out tumor cells, separated out tumor stem cells and separated out tumor breakdown products. Method 200 may comprise a step 310 of filtering the exogenous blood to obtain blood plasma. This may be performed using a centrifuge. Method 300 may also comprise a step 320 of filtering the blood plasma obtained in order to separate out at least one of the tumor cells, tumor stem cells and tumor breakdown products. This step 320 may be performed using any version of the filtration system 50 of systems 10, 100 or method 200 and with any version of method step 210 of method 200 including any substep thereof or version thereof.

In one version of method 200 or method 300, the method further comprises separating tumor exosomes 94 from the blood plasma by a step by step centrifuging process using centrifuge 57, for example after the purifying of the blood plasma 99. The step by step centrifuging process may comprise using a centrifuge 57 at a first speed, then at a second speed and then at a third speed to finally obtain the tumor exosomes. The first speed may be 750-1250 rpm (which may for example be applied for about one minute), the second speed may be 4000-6000 rpm and the third speed may be 6,000-8,000 rpm (which may for example be applied for about 3-5 minutes). These speeds and time intervals are merely illustrative and are non-limiting.

Method 300 may also include a step of using a processing unit 80 to control the filtering of the blood plasma, for example by controlling a blood filtration system 50 that implements the step of filtering the blood plasma to separate out at least one of the tumor cells, tumor stem cells and tumor breakdown products.

One implementation of method 300 involves purifying the blood plasma by removing (all three of) the tumor cells, tumor stem cells and tumor breakdown products, adding back the purified blood plasma to the blood of the patient (for example the original 200 cc) from which the blood plasma had been separated. A further version comprises also recirculating the reconstituted purified blood back into the patient (for example through the patient's veins). This process of cleaning or purifying the blood from tumor components (cells, breakdown products) may be repeated many times (for example 25 times for an average adult if 200 cc of blood is removed in each session) in some embodiments until all of the patient's blood has been purified of circulating tumor cells, tumor stem cells and tumor breakdown products.

Figure 8:
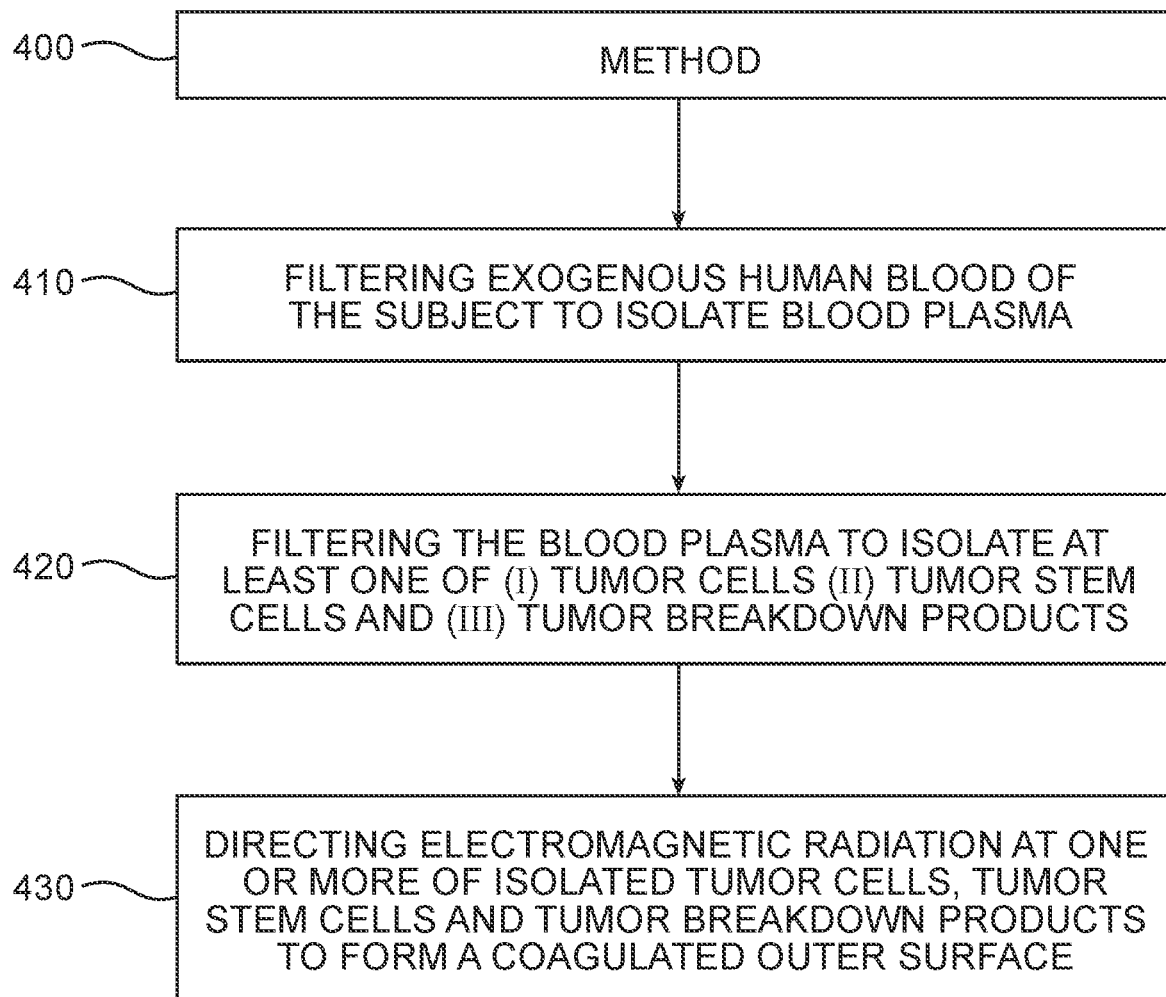
FIG. 8 is a flow chart showing a further method, in accordance with one embodiment.

As shown in FIG. 8, method 400 is a method of cleaning exogenous blood and preparing a vaccine against cancer for a mammalian subject using components of the exogenous blood. Method 400 may comprise a step 410 of filtering exogenous human blood of the subject to separate out blood plasma. The exogenous blood may be about 200 cc of blood (or another suitable amount described herein with respect to any method or system) or whatever was removed from the patient in that session. The filtering of the blood to obtain the blood plasma may occur by means of a centrifuge that takes advantage of the fact that the plasma is more liquidy than the remainder of the blood.

Method 400 may also comprise a step 420 of filtering the blood plasma to separate out an oncological component that is primarily one or more of tumor cells, tumor stem cells and tumor breakdown products. The separated out oncological component may be made up primarily of the at least one of (i) tumor cells, (ii) tumor stem cells and (iii) tumor breakdown products. The separated out oncological component may have only a remnant of blood plasma comprising in some embodiments less than about 5% by volume or less than about 1% by volume or in some embodiments less than about 0.5% by volume or in some embodiments less than about 0.1% by volume of the oncological component.

Any filtration system 50 described herein with respect to systems 10, 100 or method 200, 300 (including any version of step 210 of method 200 or step 320 of method 300) may be suitable for step 420. In some versions, one first separates the mature circulating tumor cells and then the tumor stem cells.

Method 400 may also include a step 430 of directing electromagnetic radiation at one or more of: (i) the isolated tumor cells, (ii) isolated tumor stem cells and (iii) the isolated tumor breakdown products, such as DNA, so that they acquire a coagulated outer surface or layer 91a, 92a, 93a respectively. This is the reprogramming step so that the vaccine, when injected will trigger production of autologous antibodies, as described. In some embodiments, the electromagnetic radiation has wavelengths in the UV range. In some embodiments, the UV radiation is UVC radiation. In some embodiments, the UV radiation is UVC radiation and one of UVA or UVB radiation. In one non-limiting version, the UV radiation comprises at least two of UVA radiation, UVB radiation and UVC radiation, the UVA, UVB and UVC radiation provided separately. In some embodiments, the UV radiation comprises UVA radiation, UVB radiation and UVC radiation. In some embodiments, each is applied separately for about 5-9 seconds. Any version of the reprogramming step described herein with respect to system 10 or method 200 may be used in method 400. For example, step 430 may include the application of hydrogenated water, ozone and/or freezing the one or more tumor cells, tumor stem cells and tumor breakdown products. For example, method 100 may include any version of the type or combination of types of UV radiation and the lengths of time of application of this radiation described with respect to system 10 or method 200.

Method 400 may also include a step of using a processing unit 80 to control the filtering of the blood plasma, for example by controlling a blood filtration system 50 that implements the step of filtering the blood plasma to separate out at least one of the tumor cells, tumor stem cells and tumor breakdown products.

Some implementations of method 200 or method 400 include applying electromagnetic radiation to, so as to form a coagulated outer surface of, the at least one of the tumor cells, tumor stem cells and tumor breakdown products and performing at least one of:

applying hydrogenated water having a pH of about 8 to about 10 and an oxidation-reduction potential of about −400 to −800 mV to the at least one of the isolated tumor cells, isolated tumor stem cells and isolated tumor breakdown products; and freezing the at least one of the isolated tumor cells, isolated tumor stem cells and isolated tumor breakdown products for at least five minutes.

In any version of methods 200, 300, 400, in some embodiments, one or both of the following additional steps "a)" and "b)" may also be included:

a) Prior to reprogramming the one or more of the isolated tumor cells, isolated tumor stem cells and isolated tumor breakdown products, one or more of the isolated tumor cells, isolated tumor stem cells and isolated tumor breakdown products are cloned to create a large population of the tumors cells, tumor stem cells or tumor breakdsown products by placing them in animal plasma or in the subject's own plasma, a "medium/suspension" that serves as nutrients for these isolated tumor cells, tumor stem cells and tumor breakdown products to help them grow and replicate. This growth and replication will happen naturally (although if desired other known techniques for growth and multiplication may be added). Then the reprogramming step(s) are conducted on the cloned population.

b) After the reprogramming step of any of methods 200, 300, 400, add the reprogrammed material (i.e. the one or more of tumor cells, tumor stem cells and tumor breakdown products) to antigen presenting cells (APCs) including macrophages, B cells and dendritic cells that are in solution. This can be achieved by drawing peripheral blood (of the same subject from whom the exogenous blood was taken) for example by phlebotomy and running a cycle in a centrifuge to separate the whole blood components and then taking only white blood cell (WBC) and placing these (or only the APCs within the WBCs) in a solution (suspension). This yields a faster acting vaccine since we allow the subject's exhausted immune system to skip at least one step of the process of converting the immune system from a tolerogenic (accepting) state to an immunogenic (cancer destroying) state. The immune system (once the vaccine is injected) and APCs no longer have to take the time to find the reprogrammed tumor cells, stem cells and tumor breakdown products naturally. The B cells and the T cells will be able to act immediately without having to wait for the antigen presenting cells to find the tumor cells, process the them and coupling their peptides to a surface of the immune system cells (T cells and B cells).

In any system 10, 100 or method 200, 300, 400 herein, reference to the separated out oncological component comprising at least one of or at least two of (i) the separated tumor cells, (ii) the separated tumor stem cells and (iii) the separated tumor breakdown products, or comprising (i) the separated tumor cells, (ii) the separated tumor stem cells and (iii) the separated tumor breakdown products, does not necessarily mean that these elements of the oncological component are separated from one another. In some embodiments, they are separated from one another and in some embodiments they are not separated from one another (in whole or in part).

Likewise, in any system 10, 100 or method 200, 300, 400 herein, in some implementations of the reprogramming of the separated oncological component (namely at least one of or at least two of or all of (i) the separated tumor cells, (ii) the separated tumor stem cells and (iii) the separated tumor breakdown products) these elements of the oncological component are not necessarily separated from one another. In some implementations of the reprogramming of the separated out oncological component they are not separated from one another in whole or in part and in some implementations they are separated from one another.

As used in this patent application, the term "about" may be used to specify a value of a quantity or parameter to within a continuous range of values in the neighborhood of (and including) a given (stated) value. In particular, "about" specifies the value of a parameter to be between 95% and 105% of the given value.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of preparing an autologous vaccine against cancer for a mammalian subject using components of exogenous blood of the subject and without use of a surgical invasive biopsy, the method comprising:
    using a conically arranged or conically shaped coil positioned upstream of a blood filtration system, a base of the conically arranged or conically shaped coil situated at a widest portion of the coil, the base configured to receive the exogenous blood of the subject flowing peristaltically;
    filtering, by the blood filtration system, exogenous blood plasma of the exogenous blood, the exogenous blood outputted from the conically arranged or conically shaped coil, to remove an oncological component by removing at least one of tumor cells, tumor stem cells and tumor breakdown products in at least one step and then filtering, by centrifuging, the at least one of the tumor cells, tumor stem cells and tumor breakdown products in a further step to remove tumor exosomal peptides and leave a remaining amount of tumor breakdown products, the removed tumor exosomal peptides not configured to be recognized as an antigen by an immune system of the subject; and
    converting the removed tumor exosomal peptides into an antigen by directing electromagnetic radiation at the removed oncological component, so as to convert an outer surface of the removed tumor exosomal peptides into a coagulated outer surface so as to be recognizable as the antigen by the immune system; and
    using a processing unit to control the filtering of the blood plasma.

2. The method of claim 1, wherein the removed tumor exosomal peptides has only a remnant of the blood plasma that is less than about 5% by volume of the removed tumor exosomal peptides.

3. The method of claim 1, wherein the removed tumor exosomal peptides has only a remnant of the blood plasma that is less than about 1% by volume of the removed tumor exosomal peptides.

4. The method of claim 1, wherein the removed tumor exosomal peptides has only a remnant of the blood plasma that is less than about 0.5% by volume of the removed tumor exosomal peptides.

5. The method of claim 1, further comprising removing the tumor exosomes from the exogenous blood plasma by a step by step centrifuging process after separating out the oncological component from the exogenous blood plasma.

6. The method of claim 1, further comprising degrading one or more layers of water surrounding the outer surface of the removed exosomal peptides.

7. The method of claim 1, wherein the electromagnetic radiation has wavelengths in an ultraviolet (UV) range.

8. The method of claim 1, wherein the UV radiation comprises UVC radiation.

9. The method of claim 1, further comprising irradiating the removed exosomal peptides with electromagnetic radiation of up to 0.1 terahertz.

10. The method of claim 1, further comprising after directing electromagnetic radiation at the removed exosomal peptides, injecting the removed tumor exosomal peptides into the subject to induce the subject's immune system to produce autologous antibodies in reaction to the coagulated outer surface of the removed tumor exosomal peptides.

11. The method of claim 1, further comprising separating out the oncological component from the blood plasma using a filter that has multiple layers, each layer having differently sized apertures to retain differently-sized materials from among (i) one or more sizes of the tumor cells, (ii) the tumor stem cells and (iii) the tumor exosomal peptides.

12. The method of claim 1, wherein the filtering utilizes a filter that has an outer layer configured to retain the tumor cells, the outer layer having apertures of a first diameter and has a second layer configured to retain the tumor stem cells, the second layer having apertures of a second diameter smaller than the first diameter.

13. The method of claim 12, wherein the filter further comprises an inner layer configured to retain the removed tumor exosomal peptides and apertures of a third diameter smaller than the second diameter.

14. The method of claim 1, wherein the removed oncological component comprises at least two of (i) the removed tumor cells, (ii) the removed tumor stem cells and (iii) the removed tumor breakdown products.

15. The method of claim 1, further comprising reinjecting the exogenous blood including the blood plasma into the subject without the removed tumor exosomal peptides.

16. The method of claim 1, further comprising converting at least one of the tumor cells, the tumor stem cells and the remaining amount of tumor breakdown products into an antigen by directing electromagnetic radiation at the at least one of the tumor cells, the tumor stem cells and the remaining amount of tumor breakdown products so as to convert an outer surface of at least one of the tumor cells, the tumor stem cells and the remaining amount of tumor breakdown products into a coagulated outer surface so as to be recognizable as the antigen by the immune system.

17. The method of claim 1, wherein the oncological component comprises the tumor cells, the tumor stem cells and the tumor breakdown products and further comprising directing electromagnetic radiation at the tumor cells, the tumor stem cells and the remaining amount of tumor breakdown products so as to convert an outer surface of each of the tumor cells, the tumor stem cells and the remaining amount of tumor breakdown products into a coagulated outer surface so as to be recognizable as the antigen by the immune system.

18. A method of preparing an autologous vaccine against cancer for a mammalian subject using components of autologous exogenous blood of the subject and without use of a surgical invasive biopsy, the method comprising:
using a conically arranged or conically shaped coil positioned upstream of a blood filtration system, a base of the conically arranged or conically shaped coil situated at a widest portion of the coil, the base configured to receive the autologous exogenous blood flowing peristaltically;
filtering, by the blood filtration system, exogenous blood plasma of the autologous exogenous blood outputted from the conically arranged or conically shaped coil, to remove an oncological component by filtering the exogenous blood plasma to remove at least three types of oncological components from among: (i) tumor cells, (ii) tumor stem cells, (iii) tumor exosomal peptides, (iv) tumor DNA, (v) tumor RNA, in multiple filtration steps, none of the at least three types of the oncological component recognized as an antigen by an immune system of the subject; and
converting each of the removed at least three types of oncological components into at least three types of the antigen by directing electromagnetic radiation at the removed at least three oncological components, so as to convert an outer surface of the removed at least three types of oncological components into a coagulated outer surface so as to be recognizable as at least three types of the antigen by the immune system; and
using a processing unit to control the filtering of the blood plasma.

19. The method of claim 18, further comprising injecting the at least three types of antigens into the subject to induce the subject's immune system to produce autologous antibodies in reaction to the coagulated outer surface of the removed at least three types of oncological component.

20. The method of claim 18, wherein the electromagnetic radiation has wavelengths in an ultraviolet (UV) range.

21. The method of claim 18, wherein the UV radiation comprises UVC radiation.

22. The method of claim 18, further comprising irradiating the removed exosomal peptides with electromagnetic radiation of up to 0.1 terahertz.

23. The method of claim 18, further comprising separating out the oncological component from the blood plasma using a filter that has multiple layers, each layer having differently sized apertures to retain differently-sized materials.

24. The method of claim 18, wherein the filtering utilizes a filter that has an outer layer configured to retain the tumor cells, the outer layer having apertures of a first diameter and has a second layer configured to retain the tumor stem cells, the second layer having apertures of a second diameter smaller than the first diameter, wherein the filter further comprises an inner layer configured to retain the removed tumor exosomal peptides and apertures of a third diameter smaller than the second diameter.

25. The method of claim 18, wherein the removed at least three types of oncological components comprise (i) the removed tumor cells, (ii) the removed tumor stem cells and (iii) the removed tumor exosomal peptides.

26. A method of preparing an autologous vaccine against cancer for a mammalian subject using components of autologous exogenous blood of the subject and without use of a surgical invasive biopsy, the method comprising:
using a conically arranged or conically shaped coil positioned upstream of a blood filtration system, a base of the conically arranged or conically shaped coil situated at a widest portion of the coil and configured to receive the autologous exogenous blood flowing peristaltically;
filtering, by the blood filtration system, exogenous blood plasma of the autologous exogenous blood outputted from the conically arranged or conically shaped coil to remove an oncological component comprising at least one of tumor cells, tumor stem cells and tumor breakdown products, the oncological component not recognized as an antigen by an immune system of the subject; and
converting the removed oncological component into an antigen by (i) directing electromagnetic radiation at, and (ii) applying ozonated water to, the removed oncological component so as to cause the at least one of the removed tumor cells, tumor stem cells and tumor breakdown products to have a coagulated outer surface such that the removed oncological component is altered so as to be recognizable as the antigen by the immune system.

27. The method of claim 26, wherein the electromagnetic radiation has wavelengths in an ultraviolet (UV) range.

28. The method of claim 27, wherein the UV radiation comprises UVC radiation.

\* \* \* \* \*